United States Patent
Wang

(10) Patent No.: US 12,303,016 B2
(45) Date of Patent: May 20, 2025

(54) DISINFECTION DEVICE AND TOOTHBRUSH

(71) Applicant: SHENZHEN JIBIE TECHNOLOGY CO., LTD., Shenzhen (CN)

(72) Inventor: Xin Wang, Shenzhen (CN)

(73) Assignee: GUANGDONG HUALE SCIENCE AND TECHNOLOGY DEVELOPMENT CO., LTD, Guangzhou (CN)

( * ) Notice: Subject to any disclaimer, the term of this patent is extended or adjusted under 35 U.S.C. 154(b) by 895 days.

(21) Appl. No.: 17/598,234

(22) PCT Filed: Jan. 10, 2020

(86) PCT No.: PCT/CN2020/071397
§ 371 (c)(1),
(2) Date: Sep. 24, 2021

(87) PCT Pub. No.: WO2020/192248
PCT Pub. Date: Oct. 1, 2020

(65) Prior Publication Data
US 2022/0183458 A1    Jun. 16, 2022

(30) Foreign Application Priority Data

Mar. 27, 2019  (CN) .......................... 201920399742.4
May 20, 2019  (CN) .......................... 201920722091.8
(Continued)

(51) Int. Cl.
*E04H 4/16*  (2006.01)
*A46B 17/02*  (2006.01)
(Continued)

(52) U.S. Cl.
CPC ............ *A46B 17/065* (2013.01); *A46B 17/02* (2013.01)

(58) Field of Classification Search
CPC ... A61C 3/00; A46B 9/04; A61L 2/025; A61L 2/10
(Continued)

(56) References Cited

U.S. PATENT DOCUMENTS

| 4,997,629 A | 3/1991 | Marchand et al. |
| 5,400,839 A * | 3/1995 | Cravett ................ A61C 15/043 141/357 |

(Continued)

FOREIGN PATENT DOCUMENTS

| CN | 202386084 U | 8/2012 | |
| CN | 202776617 U * | 3/2013 | ............. A61C 17/28 |

(Continued)

OTHER PUBLICATIONS

European Patent Office English Translation of CN20277661 U Descripton Section and Claims Section.*
(Continued)

*Primary Examiner* — Monzer R Chorbaji

(57) ABSTRACT

Disclosed are a disinfection device and a toothbrush having the disinfection device. The disinfection device includes a housing, a mounting portion and a disinfection portion. The housing has a first accommodating cavity within the housing and a first opening portion at an upper end of the housing, the first opening portion is communicated with the first accommodating cavity and capable of being opened or closed. The mounting portion is accommodated in the first accommodating cavity and capable of sliding in an axial direction of the first accommodating cavity. The disinfection portion is arranged in the first accommodating cavity and performs disinfection in the first accommodating cavity after the first opening portion is closed.

15 Claims, 14 Drawing Sheets

(30) Foreign Application Priority Data

| | | | |
|---|---|---|---|
| May 24, 2019 | (CN) | ......................... | 201920760663.1 |
| May 24, 2019 | (CN) | ......................... | 201920761194.5 |
| Oct. 23, 2019 | (CN) | ......................... | 201911012110.9 |
| Oct. 23, 2019 | (CN) | ......................... | 201911012122.1 |

(51) Int. Cl.
  *A46B 17/06* (2006.01)
  *A61C 15/00* (2006.01)
  *A61N 5/00* (2006.01)

(58) Field of Classification Search
  USPC ..................... 422/24, 28; 15/1.7; 433/216; 250/453.11, 454.11, 455.11, 492
  See application file for complete search history.

(56) References Cited

U.S. PATENT DOCUMENTS

| | | | |
|---|---|---|---|
| 6,135,279 A | 10/2000 | Dryer | |
| 2006/0204416 A1 | 9/2006 | Hayes et al. | |
| 2010/0233646 A1* | 9/2010 | Brokx | A61C 5/62 222/196 |
| 2015/0374467 A1 | 12/2015 | Nazeri | |
| 2018/0166904 A1* | 6/2018 | Pan | H02J 50/12 |

FOREIGN PATENT DOCUMENTS

| | | | |
|---|---|---|---|
| CN | 205625061 U | 10/2016 | |
| CN | 206443785 U | 8/2017 | |
| CN | 107280222 A | 10/2017 | |
| CN | 108552723 A | 9/2018 | |
| CN | 108813910 A | 11/2018 | |
| CN | 208301248 U | 1/2019 | |
| CN | 209347281 U | 9/2019 | |
| CN | 211242084 U | 8/2020 | |
| JP | 2013111129 A | 6/2013 | |

OTHER PUBLICATIONS

First office action issued on May 25, 2023 in Applicant's related Chinese Patent Application No. 2019110121221.1 (Publication No. CN110811120A).

First search report issued on May 23, 2023 in Applicant's related Chinese Patent Application No. 2019110121221.1 (Publication No. CN110811120A).

Second office action issued on Nov. 7, 2023 in Applicant's related Chinese Patent Application No. 2019110121221.1 (Publication No. CN110811120A).

Decision of Rejection issued on Mar. 28, 2024 in Applicant's related Chinese Patent Application No. 2019110121221.1 (Publication No. CN110811120A).

First office action issued on Apr. 22, 2022 in Applicant's related European Patent Application No. EP20778270.7 (Publication No. EP3949802).

Second office action issued on Jul. 25, 2022 in Applicant's related European Patent Application No. EP20778270.7 (Publication No. EP3949802).

* cited by examiner

DISINFECTION DEVICE AND TOOTHBRUSH

CROSS-REFERENCE TO RELATED APPLICATIONS

The present invention is filed based upon and claims benefit of Chinese Patent Applications No. 201920399742.4, filed on Mar. 27, 2019; No. 201920722091.8, filed on May 20, 2019; No. 201920761194.5, filed on May 24, 2019; No. 201920760663.1, filed on May 24, 2019; No. 201911012110.9, filed on Oct. 23, 2019; No. 201911012122.1, filed on Oct. 23, 2019; and PCT Application PCT/CN2020/071397, filed on Jan. 10, 2020; the contents of which are hereby incorporated by reference in their entirety.

TECHNICAL FIELD

The present invention relates to the technical field of daily necessities, and in particular, to a disinfection device and a toothbrush.

BACKGROUND

In people's daily life, some essential daily necessities, such as toothbrushes, spoons, and chopsticks, are indispensable. These daily necessities are usually consumable, for example, people regularly replace their toothbrushes, and thus they will not clean and disinfect the toothbrush heads of the toothbrushes. Most of the known toothbrushes are in a form of straight rod with a handle at one end and a toothbrush head at the other end, and the toothbrush head is always exposed to the environment. As a result, the exposed toothbrush head may be easily stained with dust and is difficult to be cleaned.

SUMMARY

In view of the above technical problems, the present invention provides a disinfection device and a toothbrush having the disinfection device.

The disinfection device includes a housing, having a first accommodating cavity within the housing, and a first opening portion at an upper end of the housing, and the first opening portion being communicated with the first accommodating cavity and capable of being opened or closed; a mounting portion, accommodated in the first accommodating cavity and capable of sliding in an axial direction of the first accommodating cavity; and a disinfection portion, arranged in the first accommodating cavity and performing disinfection in the first accommodating cavity after the first opening portion is closed.

In some embodiments the disinfection device further includes a second driving portion accommodated in the first accommodating cavity and connected to the mounting portion, wherein the second driving portion drives the mounting portion to slide in the axial direction of the first accommodating cavity.

In some embodiments the second driving portion includes a first sleeve, provided with an internal thread on an inner surface thereof, and the mounting portion being accommodated in the first sleeve; an external thread portion, connected to the mounting portion and engaged with the internal thread of the first sleeve; and a first motor, configured to drive the first sleeve and the external thread portion to rotate relatively.

In some embodiments, the mounting portion includes a mounting housing, the external thread portion is arranged on an outer peripheral surface of the mounting housing, and the first motor is connected to the first sleeve and drives the first sleeve to rotate.

In some embodiments, the disinfection device further includes a first guide portion including a first guide shaft and a first guide hole, where the first guide shaft is mounted to the housing and accommodated in the first accommodating cavity, the first guide hole is formed in the mounting housing, and the first guide shaft is inserted into the first guide hole.

In some embodiments, the first motor is mounted below the first sleeve, the first sleeve is provided with a first connecting piece at a lower portion thereof, and the first motor has an output shaft connected to the first connecting piece.

In some embodiments, the disinfection device further includes g a second sleeve, where the second sleeve is accommodated in the first accommodating cavity, and the first sleeve is embedded in the second sleeve.

In some embodiments, the second driving portion is provided with a first rotating part, the external thread portion is arranged on an outer peripheral surface of the first rotating part, the first motor is accommodated in the first sleeve and mounted on the mounting portion, and the first rotating part is connected to the output shaft of the first motor.

In some embodiments, the disinfection device further includes a second guide portion comprising a first guide groove and a first slider, where the first guide groove is arranged on the inner surface of the first sleeve and extends in an axial direction of the first sleeve, and the first slider is arranged on the mounting portion and capable of sliding in the first guide groove.

In some embodiments, the mounting portion includes a mounting housing having a mounting cavity in which the first motor is mounted, and the output shaft of the first motor extends out of the mounting housing.

In some embodiments, between an outer surface of the first sleeve and an inner surface of the housing, the first accommodating cavity has a third mounting space extending in the axial direction of the first accommodating cavity, and a battery is mounted in the third mounting space.

In some embodiments, the second driving portion includes a second motor, mounted on the mounting portion; and a gear and rack transmission mechanism, a rack of the gear and rack transmission mechanism being fixed in the first accommodating cavity, and a gear of the gear and rack transmission mechanism being connected to an output shaft of the second motor.

In some embodiments, the second driving portion includes a third motor, fixed in the first accommodating cavity; and a screw, at one end thereof connected to the third motor, and engaged with a screw hole provided in the mounting portion.

In some embodiments, the second driving portion includes a fourth motor, fixed in the first accommodating cavity; and a transmission belt, connected to the fourth motor and the mounting portion, respectively.

In some embodiments, the second driving portion includes a first spring, accommodated in a lower portion of the first accommodating cavity and configured to drive the mounting portion to slide toward an upper portion of the first accommodating cavity; and a clamping portion, arranged on the inner surface of the housing and configured to clamp the mounting portion when the mounting portion compresses the first spring and slides toward the lower portion of the first accommodating cavity.

In some embodiments, the disinfection portion comprises a disinfection lamp capable of emitting disinfection light, and the disinfection lamp is arranged on the upper portion of the first accommodating cavity.

In some embodiments, the disinfection lamp is a UVC band disinfection lamp.

In some embodiments, the disinfection device further includes a control board with a boosting circuit.

In some embodiments, the first accommodating cavity at two ends thereof in the axial direction are provided with limit switches respectively, and the limit switches limit a sliding stroke of the mounting portion in the axial direction of the first accommodating cavity.

In some embodiments, the limit switch is at least one of a Hall switch, a contact mechanical switch and a photoelectric switch.

In some embodiments, when the mounting portion axially slides in a direction towards the first opening portion, at least part of the mounting portion drives the first opening portion to open and extends out of the first accommodating cavity.

In some embodiments, the disinfection device further includes an upper cover portion, where the upper cover portion is arranged at the upper end of the housing and configured to be capable of opening or closing the first opening portion; where the upper cover portion comprises a hinge pin, a first cover body, a second cover body and second springs; where the hinge pin is mounted at the upper end of the housing, and the first cover body and the second cover body are respectively hinged to the hinge pin and rotatable around the hinge pin to approach or move away from each other; and where there the second springs comprises two second springs, one of the second springs abuts against the upper end of the housing and the first cover body, another one of the second springs abuts against the upper end of the housing and the second cover body, and the two second springs respectively push the first cover body and the second cover body to be close to each other.

The toothbrush includes a toothbrush head; and the disinfection device, where the toothbrush head is mounted on the mounting portion; where, when the mounting portion slides towards the upper portion inside the first accommodating cavity, the toothbrush head drives the first opening portion to be opened and extends to the exterior of the housing; and where, when the mounting portion slides toward the lower portion of the first accommodating cavity, the toothbrush head retracts from the exterior of the housing into the first accommodating cavity and closes the first opening portion.

In some embodiments, the toothbrush further includes a first driving portion mounted in the mounting portion, wherein the toothbrush head is detachably mounted on the first driving portion.

In some embodiments, the first driving portion is provided with a vibration motor, and the toothbrush head is detachably mounted on an output shaft of the vibration motor.

In some embodiments, the toothbrush further includes a first contact and a second contact provided in the upper portion of the first accommodating cavity; where the mounting portion further comprises a first electrode and a second electrode respectively connected to the first driving portion; and where, when the mounting portion slides to the upper portion of the first accommodating cavity, the first electrode is in contact with the first contact, and the second electrode is in contact with the second contact.

In some embodiments, the first contact and the second contact are spring piece contacts capable of clamping the first electrode and the second electrode, respectively.

With the disinfection device of the present invention, the daily necessities such as a toothbrush can be accommodated in the first accommodating cavity and disinfected there.

DESCRIPTION OF EMBODIMENTS

Figure 1:
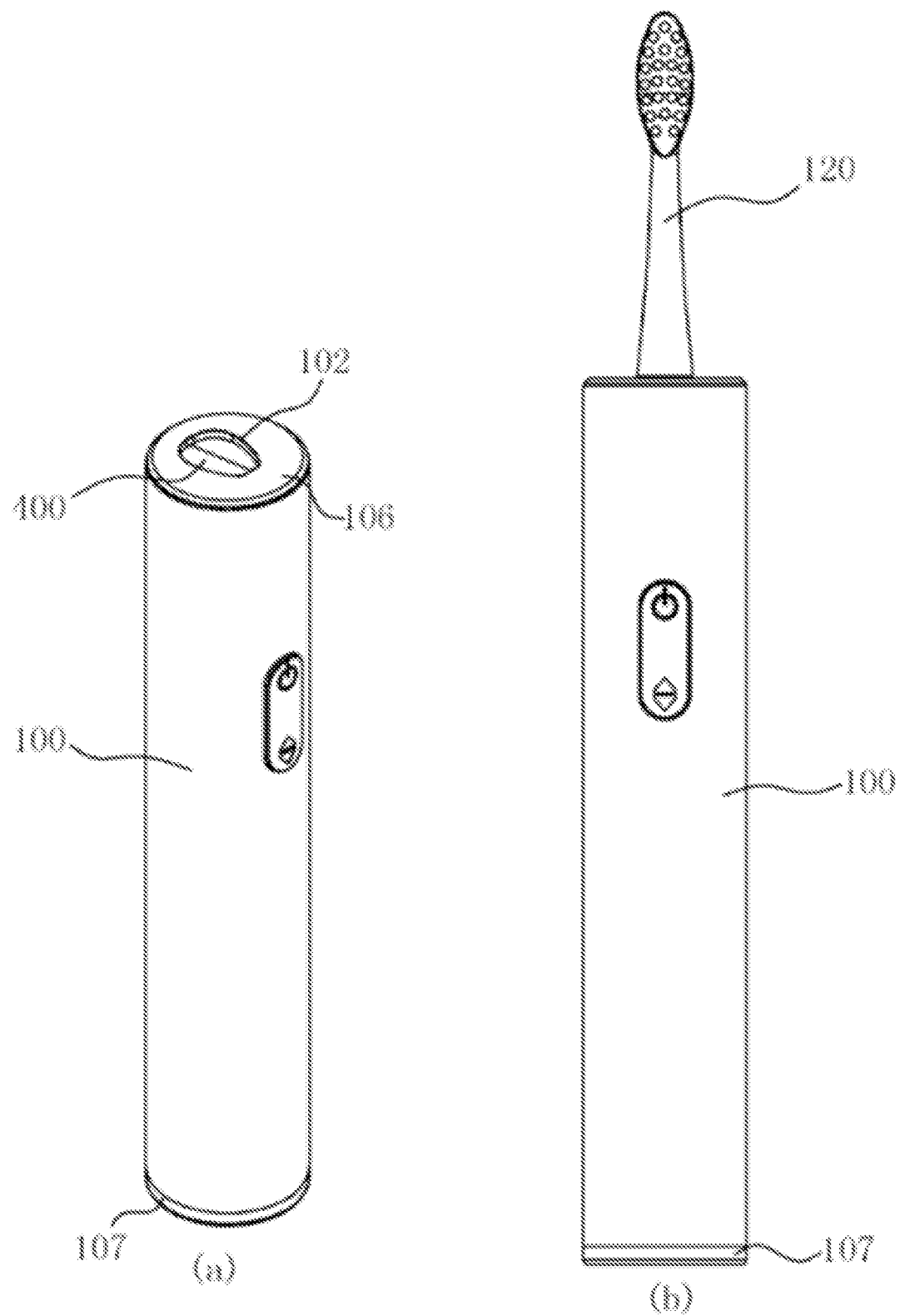
FIG. 1 is a schematic view of a disinfection device according to an embodiment of the present invention, where (a) is a schematic view of the disinfection device with a first opening portion being closed, and (b) is a schematic view of the disinfection device (toothbrush) equipped with a toothbrush head.

Embodiments of the present invention will be described in detail below. Examples of the embodiments are shown in the accompanying drawings, in which the same or similar reference numerals refer to the same or similar elements or elements having the same or similar functions throughout. The embodiments described below by referring to the accompanying drawings are examples and are merely intended to explain the present invention, and cannot be understood as limiting the present invention.

In the description of the present invention, it should be understood that if orientation description is involved, the orientation or position relationship indicated by, for example, "up", "down", "front", "rear", "left" and "right" is based on the orientation or position relationship shown in the drawings, and these terms are just used to facilitate description of the present invention and simplify the description, but not to indicate or imply that the mentioned device or elements must have a specific orientation and must be established and operated in a specific orientation, and thus, these terms cannot be understood as a limitation to the present invention.

In the description of the present invention, "several" means one or more, and "a plurality or means more than two. "Greater than", "less than", "exceeding, and the like" are understood as excluding this number, and "above", "below", "within", and the like are understood as including this number. "First" and "second" in description are only for the purpose of" distinguishing technical features, and cannot be understood as indicating or implying relative importance or implicitly indicating the number of technical features indicated or implicitly indicating the sequence relationship of indicated technical features.

In the description of the present invention, unless otherwise explicitly defined, the words such as "setting", "mounting" and "connection" should be understood in a broad sense, and those skilled in art can properly determine the specific meanings of the above words in the present invention with reference to the specific contents of the technical solution.

Figure 2:
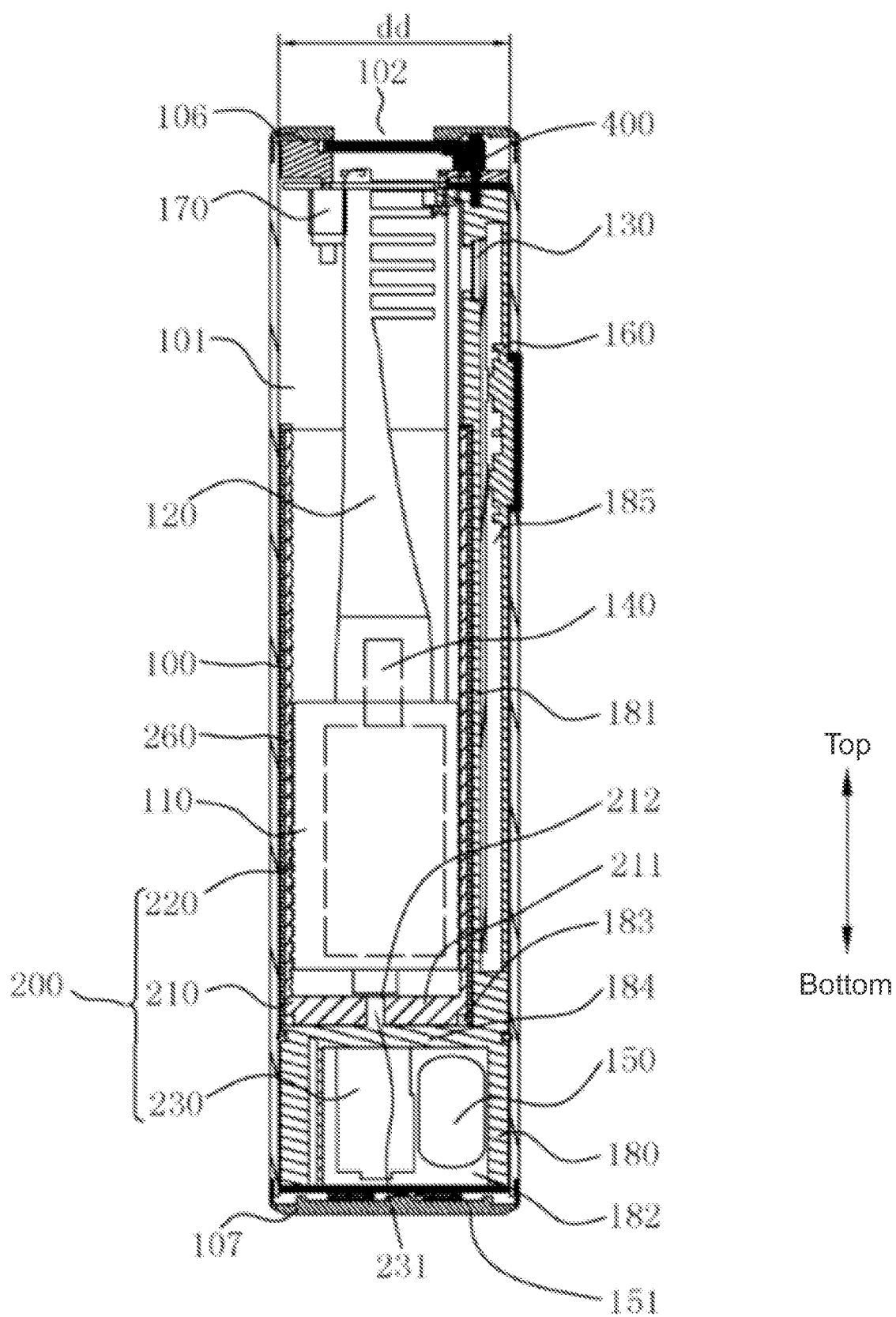
FIG. 2 is a schematic view of an internal structure of a disinfection device according to Embodiment 1.
Figure 3:
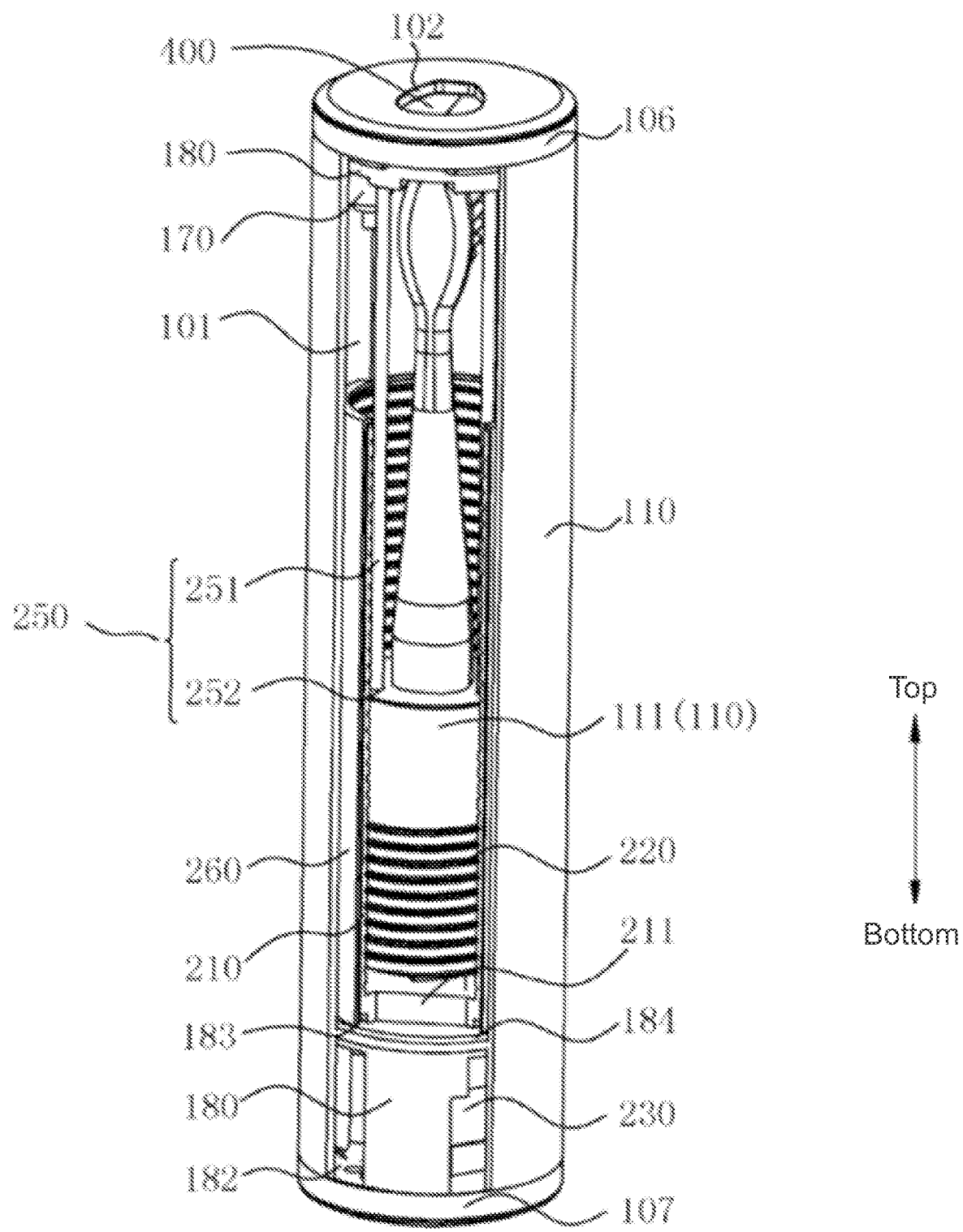
FIG. 3 is a partial sectional view of the internal structure of the disinfection device according to Embodiment 1 from another perspective.
Figure 4:
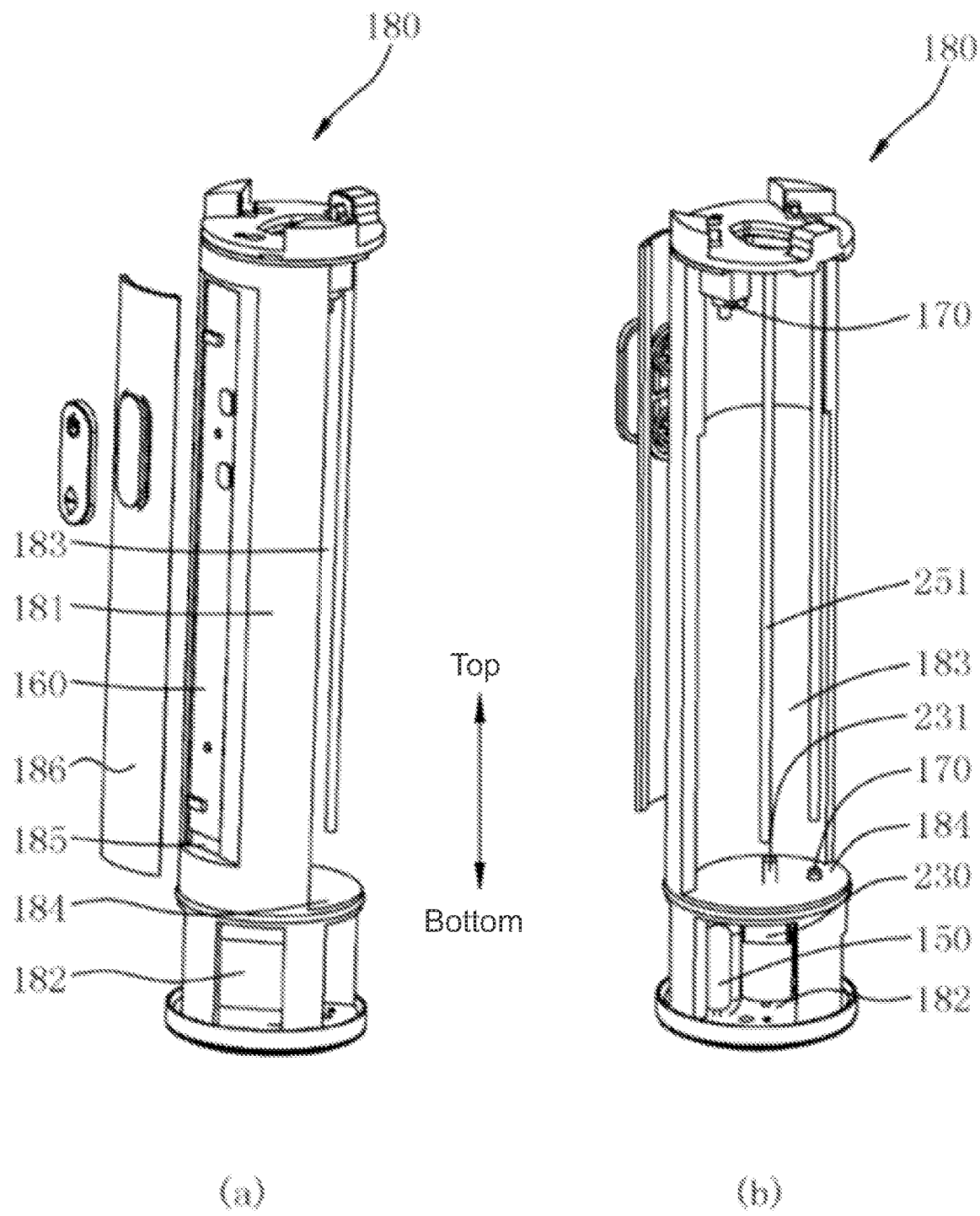
FIG. 4 is a schematic view of a base, where (a) is a schematic view from one perspective, and (b) is a schematic view from another perspective.

FIG. 1 is a schematic view of a disinfection device in an embodiment the present invention, where (a) is a schematic view showing the disinfection device where a first opening portion 102 is closed, and (b) is a schematic view showing the disinfection device for disinfecting a toothbrush head 120 where the toothbrush head 120 extends out from the disinfection device. FIG. 2 is a schematic view showing the internal structure of a disinfection device according to Embodiment 1. In order to facilitate the description of the working process of the disinfection device, disinfection on the toothbrush head 120 is taken as an example for the description. FIG. 3 is a partial sectional view showing the internal structure of the disinfection device according to Embodiment 1 from another perspective. FIG. 4 is a schematic view of a base 180, where (a) is a schematic view from one perspective, and (b) is a schematic view from another perspective. Referring to FIG. 1 to FIG. 4, the disinfection device according to this embodiment can disinfect daily necessities such as the toothbrush head 120 and a spoon (not shown). During disinfection, the toothbrush head 120 (or the spoon, or the like) retracts into the disinfection device for disinfection, and during normal use, the toothbrush head 120 extends out from the disinfection device, so the disinfection device can be used as a toothbrush since the disinfection device is equipped with a toothbrush head.

Specifically, the disinfection device includes a housing 100 that may be cylindrical or drum-shaped. The housing 100 has a first accommodating cavity 101, preferably the first accommodating cavity 101 has a substantially circular cross section, and the first accommodating cavity 101 runs through one end of the housing 100 in an axial direction for facilitating mounting of various components. A first opening portion 102 capable of being opened or closed is provided at an upper end of the housing 100, and the first opening portion 102 is communicated with the first accommodating cavity 101. Specifically, the housing 100 at one end in the axial direction is provided with an upper housing 106, where the first opening portion 102 is disposed. The upper housing 106 can be mounted at the end of the housing 100 in the axial direction through a known structure such as a buckle structure or an interference mounting structure. the housing 100 in the axial direction at the other end is provided with a lower housing 107. Similarly, the lower housing 107 can also be mounted at the other end of the housing 100 in the axial direction through a known structure such as a buckle structure or an interference mounting structure.

A battery 150, a control board 160, a mounting portion 110, a disinfection portion 130, and the like are accommodated in the first accommodating cavity 101. The battery 150 is configured to supply power to the mounting portion 110, the disinfection portion 130, the control board 160, and the like, and the control board 160 may be a PCB known to those skilled in the art. The mounting portion 110 is accommodated in the first accommodating cavity 101 and can slide in the axial direction of the first accommodating cavity 101. The toothbrush head 120 (or the spoon, or the like) is detachably mounted on an upper portion of the mounting portion 110. The mounting portion 110 slides along the axis of the first accommodating cavity 101, such that the toothbrush head 120 can extends out from the housing 100 through the first opening portion 102 or retracts into the housing 100, i.e. into the first accommodating cavity 101. When the toothbrush head 120 actuates the first opening portion 102 to open and extends out from the first accommodating cavity 101, a user can brush teeth with the toothbrush head 120. When the toothbrush head 120 retracts into the first accommodating cavity 101 through the first opening portion 102, the first opening portion 102 is closed, and after the first opening portion 102 is closed, the disinfection portion 130 can disinfect the toothbrush head 120. In order to facilitate mounting of the toothbrush head 120 or other daily necessities, for example mounting a spoon on the mounting portion 110, when the mounting portion 110 is configured to slide in the axial direction of the first accommodating cavity 101 toward the first opening portion 102, at least part of the mounting portion 110 can actuate the first opening portion 102 to open and extend out of the first accommodating chamber 101, providing convenience for dismantling and mounting the toothbrush head 120 outside the first accommodating cavity 101.

The disinfection portion 130 may include a disinfection lamp capable of emitting disinfection light, such as a disinfection lamp emitting ultraviolet light in UVC band. The disinfection lamp may be arranged at any position where the toothbrush head 120 located in the first accommodating cavity 101 can be disinfected. For example, the disinfection lamp may be mounted on an inner surface of the housing 100, and arranged opposite to the toothbrush head 120 when the toothbrush head 120 retracts into the first accommodating cavity 101, to disinfect a front face of the toothbrush head 120. In addition, the control board 160 not only includes a known control circuit for controlling, for example, a motor, but also includes a boosting circuit for boosting the voltage of the disinfection lamp for controlling ultraviolet light emitting in UVC band, for example, boosting the voltage of the circuit for controlling the disinfection lamp to 6.5 V to make the disinfection lamp work better.

Therefore, the toothbrush head, the spoon, and the like can be mounted on the disinfection device according to this embodiment. Because the toothbrush head, the spoon, and the like can be retracted into the first accommodating cavity 101 of the housing 100, the toothbrush head 120 may be not easily stained with dust. In addition, because the toothbrush head 120 is disinfected by the disinfection portion 130 in the first accommodating cavity 101, the toothbrush head, the spoon, and the like can be thoroughly cleaned, whereby bacteria, viruses, and the like generated on the toothbrush head, the spoon, and the like due to long-term humidity, and the like are killed, the service lives of the toothbrush head, the spoon, and the like are prolonged, and the oral health of the user is maintained. It should be noted that although the disinfection device is described herein, when the daily necessities, for example, a toothbrush, is mounted on the disinfection device, the disinfection device can be used as a toothbrush with the capability of disinfection, offering convenience for the user to store and disinfect the toothbrush head after use every time, and offering convenience for the user to carry the disinfection device. In addition, it is appreciated that, any known mounting structure, such as a mounting shaft and a mounting buckle, can be uses in the upper end of the mounting portion 110 for fixing the. Accordingly, the toothbrush head or spoon can be provided with a mounting hole or a mounting buckle, and the like for mounting them on the mounting portion 110.

Figure 8:
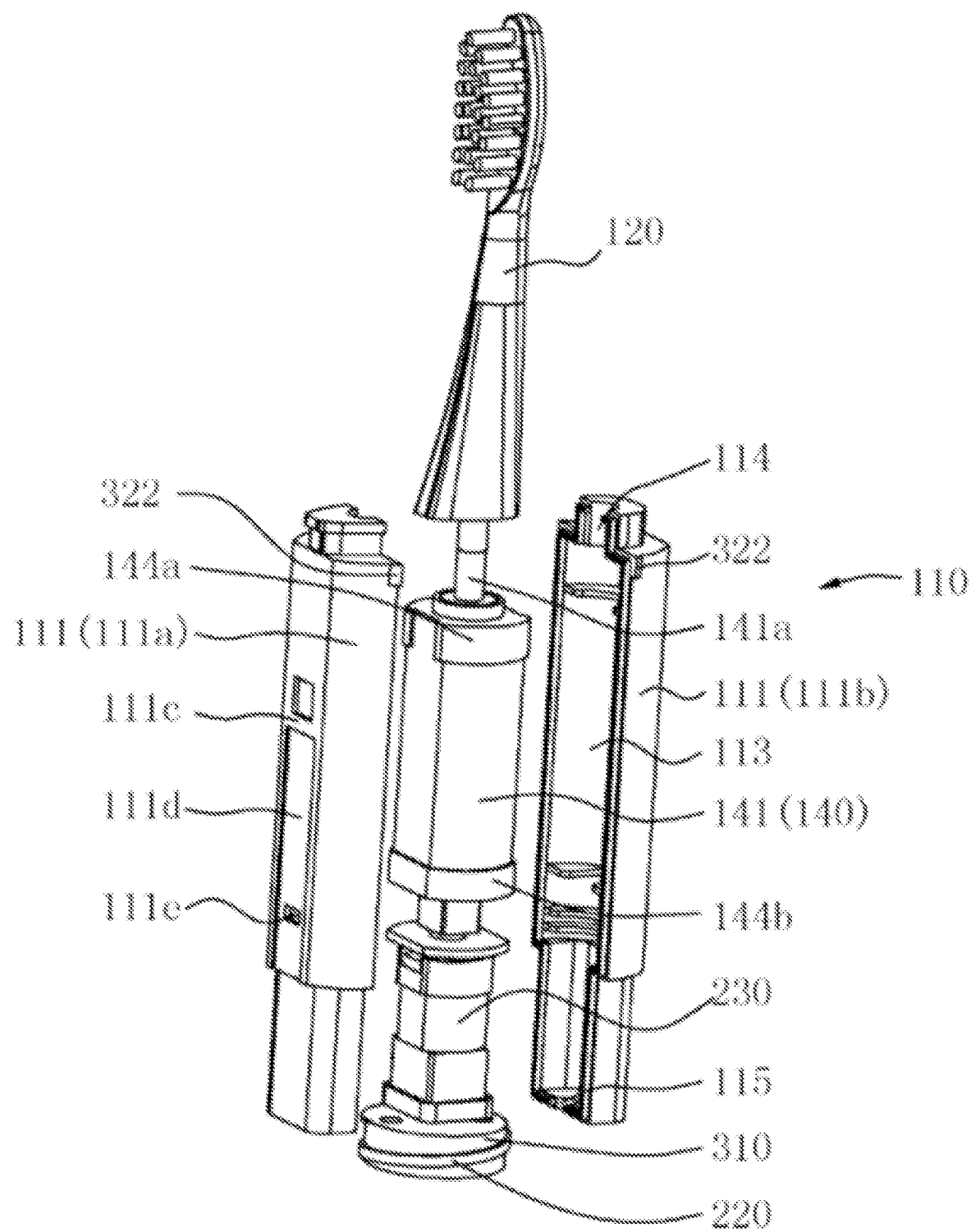
FIG. 8 is an exploded view of the mounting portion according to Embodiment 2.

FIG. 8 is an exploded view of the mounting portion 110, referring to FIG. 8, when the mounting portion 110 of the disinfection device is equipped with a toothbrush head 120, which can be used as a toothbrush capable of being disinfected, the toothbrush can have the function as an electric toothbrush. Specifically, the toothbrush includes a first driving portion 140 that is mounted in the mounting portion 110, and the toothbrush head 120 is detachably mounted on the first driving portion 140. Specifically, the mounting portion 110 includes a mounting housing 111, which can be made of wear-resistant materials, for example, plastic materials such as fluoroplastics, nylon, POM, PEEK and PET, or ceramics and plastic materials with ceramic coating on surface. Alternatively, the mounting housing 111 can be made of metal materials commonly used for making hardware parts, for example, stainless steel such as SUS303/SUS304, copper, alloy steel, chrome-plated steel parts and bearing steel. A mounting cavity 113 is formed in the mounting housing 111, specifically, the mounting housing 111 includes a first half housing 111a and second half housing 111b that are substantially semi-circular and thin-walled. The first half housing 111a and the second half housing 111b are spliced to form a complete mounting housing 111, and the mounting cavity 113 is formed in the mounting housing 111. The first driving portion 140 is mounted in the mounting cavity 113 of the mounting portion 110, specifically the first driving portion 140 is mounted on the upper portion of the mounting cavity 113, and the toothbrush head 120 is detachably connected to the first driving portion 140. The first driving portion 140 includes a vibration motor 141, which may be a known vibration motor 141 used in an electric toothbrush. The vibration motor 141 is mounted on the upper portion of the mounting cavity 113, and a first avoidance hole 114 is provided in the upper portion of the mounting cavity 113. An output shaft 141a of the vibration motor 141 extends out from the mounting housing 111 through the first avoidance hole 114 of the mounting cavity 113. Two ends of the main body of the vibration motor 141 can be covered by buffer sleeves 144a and 144b, which can be made of silica gel, rubber, and the like. The vibration motor 141 is mounted in the mounted cavity 113 through the buffer sleeves 144a and 144b. The buffer sleeves 144a and 144b between the vibration motor 141 and the mounting cavity 113 can reduce the vibration sense of the vibration motor 141, and can be used as a sealing structure to prevent water stains and the like from entering the mounting cavity 113. The toothbrush head 120 is detachably mounted on the output shaft 141a of the vibration motor 141. As such, the disinfection device according to this embodiment can not only disinfect the toothbrush head 120, prolong the service life of the toothbrush head 120, and promote the oral health of the user, but also serve as an electric toothbrush, which can further facilitate the user to use the toothbrush and further to maintain the oral health of the user.

As described above, as according to this embodiment the mounting portion 110 is accommodated in the first accommodating cavity 101 and can slide in the axial direction of the first accommodating cavity 101, the toothbrush head 120 mounted on the mounting portion 110 extends out to the exterior of the housing 100 through the first opening portion 102 or retracts from the exterior of the housing 100 into the first accommodating cavity 101 through the first opening portion 102 with the axially sliding of the mounting portion 110. Specifically, the toothbrush according to this embodiment further includes a second driving portion 200 accommodated in the first accommodating cavity 101, and the second driving portion 200 is connected to the mounting portion 110 and drives the mounting portion 110 to slide in the axial direction of the first accommodating cavity 101.

Various embodiments of the second driving portion 200 are described in detail below.

Embodiment 1

With continued reference to FIG. 2 to FIG. 4, the second driving portion 200 is provided with a first sleeve 210, an external thread portion 220, and a first motor 230. The first sleeve 210 may be made of plastic materials such as fluoroplastic, nylon, POM, PEEK and PET, ceramic, plastic materials with ceramic coating on surface, and metal materials commonly used for making hardware parts, for example, stainless steel such as SUS303/SUS304, copper, alloy steel, chrome-plated steel parts and bearing steel. an internal thread is provided with on an inner surface of the first sleeve 210, the mounting portion 110 is accommodated in the first sleeve 210, the external thread portion 220 is connected to the mounting portion 110, and the external thread portion 220 is engaged with the internal thread of the first sleeve 210. The first motor 230 may be a stepping motor, and is configured to drive the first sleeve 210 and the external thread portion 220 to rotate relatively.

Considering offering convenience for the user to hold the disinfection device, the diameter of the disinfection device according to this embodiment is preferably about 25 mm. For example, the inner diameter dd of the first accommodating cavity 101 of the disinfection device according to this embodiment is about 25 mm to 30 mm. In this embodiment, the first sleeve 210 with the internal thread is provided and the mounting portion 110 is accommodated in the first sleeve 210, the mean diameter of the internal thread of the first sleeve 210 and the mean diameter of the external thread portion 220 can be increased as far as possible in a narrow space, so that the carrying capacity of the whole external thread portion 220 for the mounting portion 110 can be improved. Through the braking force of the first motor 230 on the threaded transmission mechanism (that is, the engagement between the internal thread of the first sleeve 210 and the external thread portion 220), it can be ensured that the mounting portion can be stably stopped when the disinfection device with the toothbrush head is in use (teeth brushing), thereby preventing the mounting portion from shaking.

The thread of the external thread portion 220 and the internal thread of the first sleeve 210 may be rectangular threads, trapezoidal threads, triangular threads, zigzag threads or other threads with special shapes. The rectangular thread or the trapezoidal thread is preferred, and the mounting portion 110 can be further stably stopped by the self-locking nature of the rectangular thread or the trapezoidal thread.

In this embodiment, the external thread portion 220 is arranged on an outer peripheral surface of the mounting housing 111, that is, the external thread is provided on the outer peripheral surface of the mounting housing 111, and the first motor 230 is connected to the first sleeve 210 and drives the first sleeve 210 to rotate. The first motor 230 is fixed to the lower portion of the first accommodating cavity 101 and located below the first sleeve 210. In the lower portion of the first sleeve 210 a first connecting piece 211 is provided, and an output shaft 231 of the first motor 230 is connected to the first connecting piece 211. For example, the first sleeve 210 penetrates through only one end (upper portion) in the axial direction, and does not penetrate through the other end (lower portion) in the axial direction. The non-penetrating end of the first sleeve 210 is used as the first connecting piece 211, the first connecting piece 211 is provided with a connecting hole 212, and the output shaft 231 of the first motor 230 is inserted into the first connecting hole.

In order to facilitate dismantling and mounting of various components in the first accommodating cavity 101, the toothbrush according to this embodiment further includes a base 180, the base 180 is accommodated in the first accommodating cavity 101, and the length of the base 180 in the axial direction is slightly less than the length of the housing 100 in the axial direction. An arc-shaped main housing 181 is arranged at one side of the base 180 in the radial direction, and an outer arc surface of the main housing 181 and an inner circumferential surface of the first accommodating cavity 101 substantially fit. In a lower portion of the base 180 a first mounting space 182 is formed, in an upper portion of the base 180 a second mounting space 183 is formed, and a partition plate 184 is arranged between the first mounting space 182 and the second mounting space 183. The first motor 230 and the battery 150 are mounted below the partition plate 184 and located in the first mounting space 182.

In this embodiment, in order to position the rotation of the first sleeve 210 and prevent the first sleeve 210 from deflecting, a second sleeve 260 with both ends opened in the axial direction is also arranged in the first accommodating cavity 101, and the first sleeve 210 is inserted (in clearance fit) into the second sleeve 260. When the first motor 230 drives the first sleeve 210 to rotate, the first sleeve 210 rotates within the second sleeve 260. The second sleeve 260 may also be made of wear-resistant materials, for example, plastic materials such as fluoroplastics, nylon, POM, PEEK and PET, ceramic parts, plastic materials with ceramic coating on the surface, chromium-plated metal parts or rust-proof metal parts such as stainless steel (SUS304) and copper. The second sleeve 260 is fixed in the second mounting space 183, and the first sleeve 210 is rotatably mounted in the second sleeve 260. The output shaft 231 of the first motor 230 extends into the second mounting space 183 through the partition plate 184, and in the second mounting space 183, the first sleeve 210 is connected to the output shaft 231 of the first motor 230. It can be understood that although the example of positioning the rotation of the first sleeve 210 by providing the second sleeve 260 has been described above, it is not limited to this. For example, the first sleeve 210 can also be directly mounted in the second mounting space 183 of the base 180, and accordingly, the inner circumferential surface of the main housing 181 is configured to perform rotating positioning on the first sleeve 210.

In order to convert the relative rotation between the first sleeve 210 and the mounting portion 110 into the axial linear sliding of the mounting portion 110, in this embodiment, a first guide portion 250 is further provided. The first guide portion 250 comprises a first guide shaft 251 and a first guide hole 252. The first guide shaft 251 may be made of metal materials, such as metal materials commonly used for manufacturing hardware parts, for example, stainless steel such as SLIS303/SUS304, copper materials, alloy steel, forged steel parts, bearing steel. The first guide shaft 251 is mounted to the housing 100 and accommodated in the first accommodating cavity 101. Specifically, in this embodiment, the first guide shaft 251 extends into the first sleeve 210 in the axial direction of the first accommodating cavity 101. It can be understood that herein, the description of mounting the first guide shaft 251 on the housing 100 does not mean that the first guide shaft 251 must be directly mounted on the housing 100, and the first guide shaft 251 may alternatively be mounted on any component, (such as the base 180) that is relatively fixedly connected to the housing 100. The first guide hole 252 is formed in the mounting housing 111, and the first guide shaft 251 is inserted into the first guide hole 252, so that when the first motor 230 drives the first sleeve 210 to rotate, the mounting portion 110 slides linearly along the first guide shaft 251. Certainly, this embodiment only illustrates the first guide portion 250 by way of example, and does not limit it. Any proper mechanism that can guide a linear transmission mechanism driven by the motor can be used.

In this embodiment, in order to mount the control board 160 more conveniently, an accommodating groove 185 for accommodating the control board 160 may be formed in the main housing 181 of the base 180. In order to prevent water stains and the like from entering into the accommodating groove 185, a sealing cover 186 made of silica gel may also be provided to cover the accommodating groove 185.

Embodiment 2

Figure 5:
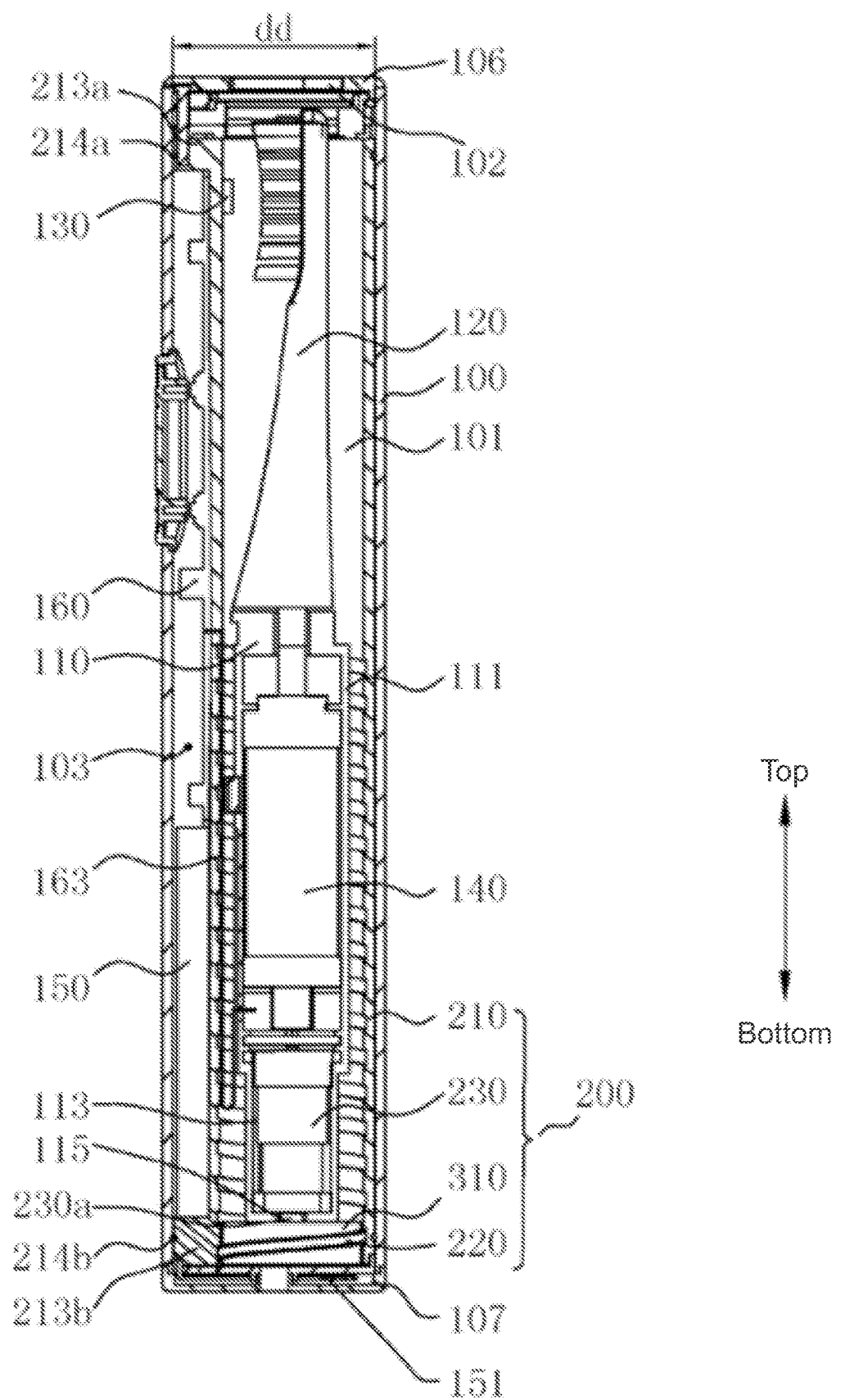
FIG. 5 is a schematic view of an internal structure of a disinfection device according to Embodiment 2.
Figure 6:
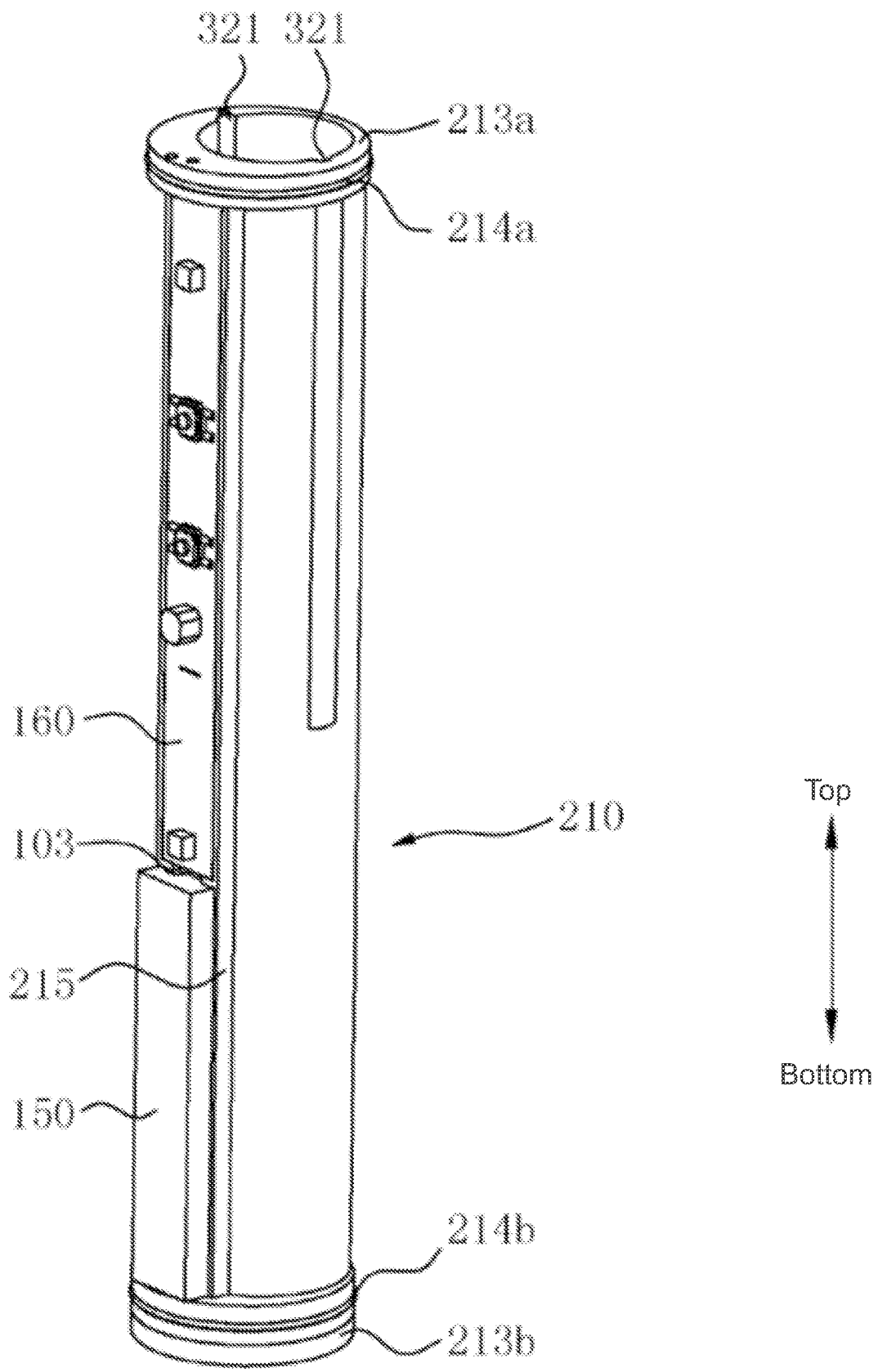
FIG. 6 is a perspective view of a first sleeve according to Embodiment 2.
Figure 7:
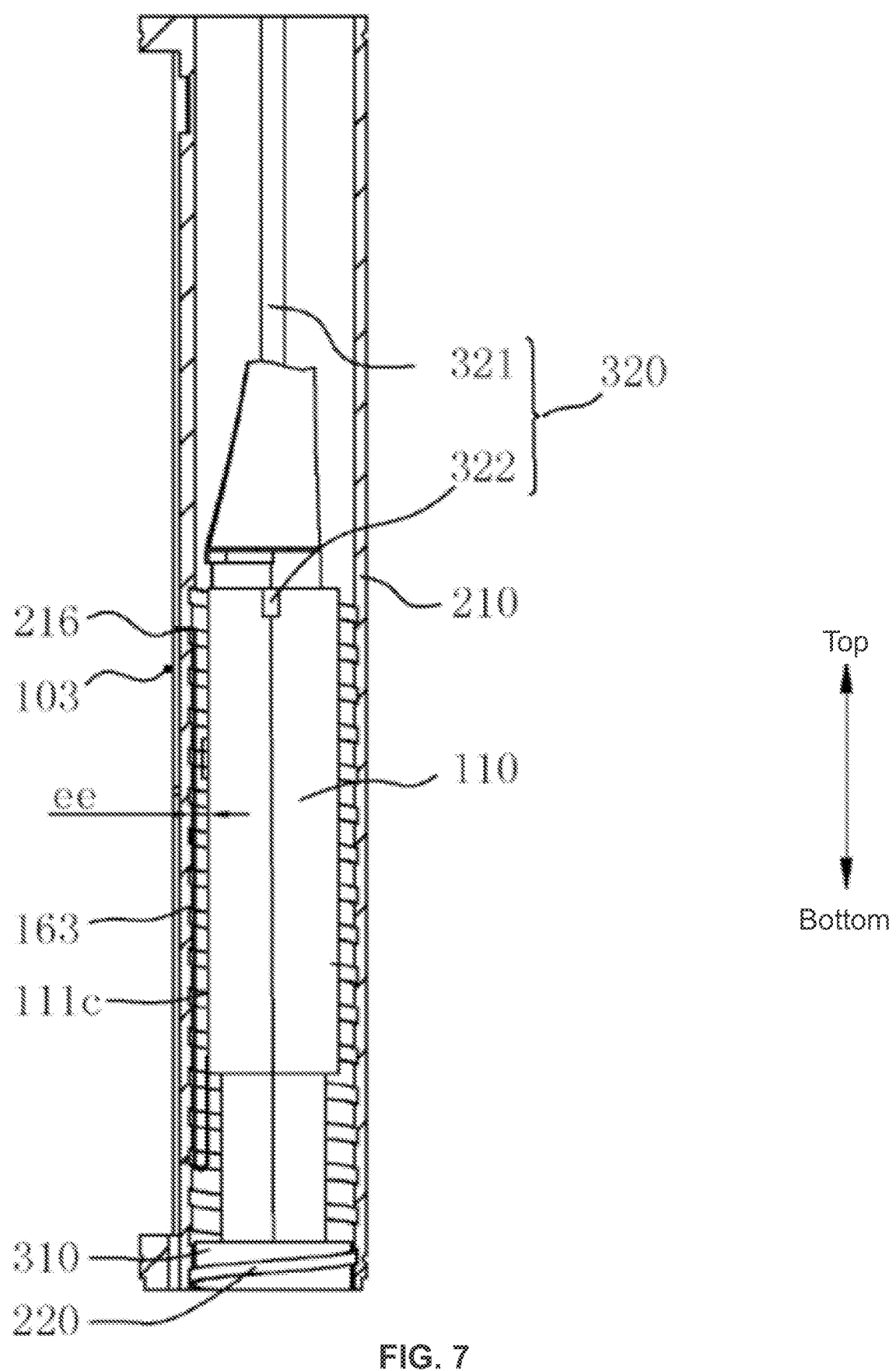
FIG. 7 is a schematic view of the interior of the first sleeve and a mounting portion in an assembled state according to Embodiment 2.

FIG. 5 is a schematic view showing an internal structure of a disinfection device for disinfecting the toothbrush head 120 according to Embodiment 2. FIG. 6 is a perspective view of a first sleeve 210 of Embodiment 2. FIG. 7 is a schematic view of the interior of the first sleeve 210 and a mounting portion in an assembled state according to Embodiment 2. FIG. 8 is an exploded view of a mounting portion 110. Referring to FIG. 5 to FIG. 8, Embodiment 2 is similar to Embodiment 1, and the difference is that in Embodiment 2, the first sleeve 210 is a fixed part, while the external thread portion 220 is a rotating part. In the following description, the technical features described in Embodiment 1 will not be repeated.

In this embodiment, the second driving portion 200 is further provided with a first rotating part 310, the external thread portion 220 is arranged on an outer peripheral surface of the first rotating part 310, the first motor 230 is accommodated in the first sleeve 210 and mounted in the mounting portion 110, and the first rotating part 310 is connected to the output shaft of the first motor 230. Specifically, the first motor 230 is also mounted in the mounting cavity 113, the vibration motor 141 is mounted in the upper portion of the mounting cavity 113, and the first motor 230 is mounted in the lower portion of the mounting cavity 113. The mounting housing 111 is provided with a second avoidance hole 115 at the bottom thereof, an output shaft 230a of the first motor 230 extends out to the exterior of the mounting housing 111 through the second avoidance hole 115, and the first rotating part 310 is located on the lower portion of the mounting portion 110 and connected to the output shaft 230a of the first motor 230.

In this embodiment, the first sleeve 210 with the internal thread is provided and the mounting portion 110 is accommodated in the first sleeve 210, the mean diameter of the internal thread of the first sleeve 210 and the mean diameter of the first rotating part 310 (the external thread portion 220) can be increased as far as possible in a narrow space, so that the accommodating capacity of the whole first rotating part 310 for the mounting portion 110 can be improved. Through the braking force of the first motor 230 on a threaded transmission mechanism (that is, the engagement between the internal thread of the first sleeve 210 and the first rotating part 310), it can be ensured that the mounting portion can be stably stopped when the disinfection device with the toothbrush head is in use (teeth brushing), thereby preventing the mounting portion from shaking.

The length of the first sleeve 210 in the axial direction is slightly less than the length of the housing 100 in the axial direction. Flanges 213a and 213b are arranged at both ends of the first sleeve 210 in the axial direction respectively, and sealing rings 214a and 214b are nested in the flanges 213a and 213b in the circumferential direction, respectively. The first sleeve 210 is embedded into the housing 100 through the sealing rings 214a and 214b, that is, the first sleeve 210 is entirely accommodated in the first accommodating cavity 101. The first sleeve 210 is provided with an internal thread on its inner surface, and accordingly, the mounting portion 110, the first motor 230 and the first rotating part 310 are respectively accommodated in the first sleeve 210, and the external thread of the first rotating part 310 is engaged with the internal thread of the first sleeve 210.

In order to convert the relative rotation between the first sleeve 210 and the mounting portion 110 into the axial linear sliding of the mounting portion 110, in this embodiment, the disinfection device further includes a second guide portion 320 that is provided with a first guide groove 321 and a first slider 322, where the first guide groove 321 is arranged on the inner surface of the first sleeve 210 and extends in an axial direction of the first sleeve 210, the first slider 322 is arranged on the mounting portion 110 and, for example, is directly integrally formed on the mounting housing 111, and the first slider 322 slides in the first guide groove 321. Therefore, by providing the first guide groove 321 and the first slider 322 as the second guide portion 320, the mounting portion 110 can be guided only by changing existing parts. This leads to a compact structure, and no additional parts are needed. Certainly, this embodiment only illustrates the second guide portion 320 by way of example, and does not limit it. Any proper mechanism that can guide a linear transmission mechanism driven by the motor can be used.

In this embodiment, between an outer surface of the first sleeve 210 and an inner surface of the housing 100, the first accommodating cavity 101 has a third mounting space 103 extending in the axial direction of the first accommodating cavity 101, and a battery 150 and a control board 160 are mounted in the third mounting space 103. The battery 150 supplies power to the control board 160, and the control board 160 is electrically connected to the vibration motor 141, the disinfection portion 130, the first motor 230 of the second driving portion 200, and the like. Specifically, a first mounting frame 215 can be arranged on the periphery of the first sleeve 210 in a protruding manner in the radial direction, and the battery 150 and the control board 160 are respectively placed in the first mounting frame 215 and fixed. In addition, the first sleeve 210 is further provided with a first wiring hole 216, the first wiring hole 216 is respectively communicated with the third mounting space 103 and the inner surface of the first sleeve 210, and configured to guide wires 163 (such as power lines and control lines) communicated with the control board 160 from the third mounting space 103 to the mounting portion 110.

In this embodiment, because the first motor 230 moves linearly with the mounting portion 110 in the first sleeve 210, the wires 163 (such as power wires and control wires) electrically connected to the first motor 230 also travel with the mounting portion 110. In order to reserve enough space for the wires 163 to travel, the mounting housing 111 is roughly rounded with a cut edge at its circumference, for example, the periphery of the mounting housing 111 is provided with a flat section 111c, and a distance ee between the flat section 111c and the inner surface of the first sleeve 210 is, for example, 5-10 mm Through the arrangement of the flat section 111c, a gap can be formed between the mounting housing 111 and the inner surface of the first sleeve 210, so as to allow the wires 163 to slide freely in the gap and prevent the wires 163 from being broken. In order to prevent the wires 163 from deflecting during traveling, a limiting frame 111d for limiting the deflection of the wires 163 may also be arranged in the gap. In addition, the flat section 111c is provided with a second wiring hole 111e, and the second wiring hole 111e is communicated with the mounting cavity 113. The wires with one end electrically connected to the control board 160 enter the mounting cavity 113 through the first wiring hole 216 and the second wiring hole 111e respectively, and are electrically connected to the vibration motor 141 and the first motor 230, respectively.

Embodiment 3

Figure 9:
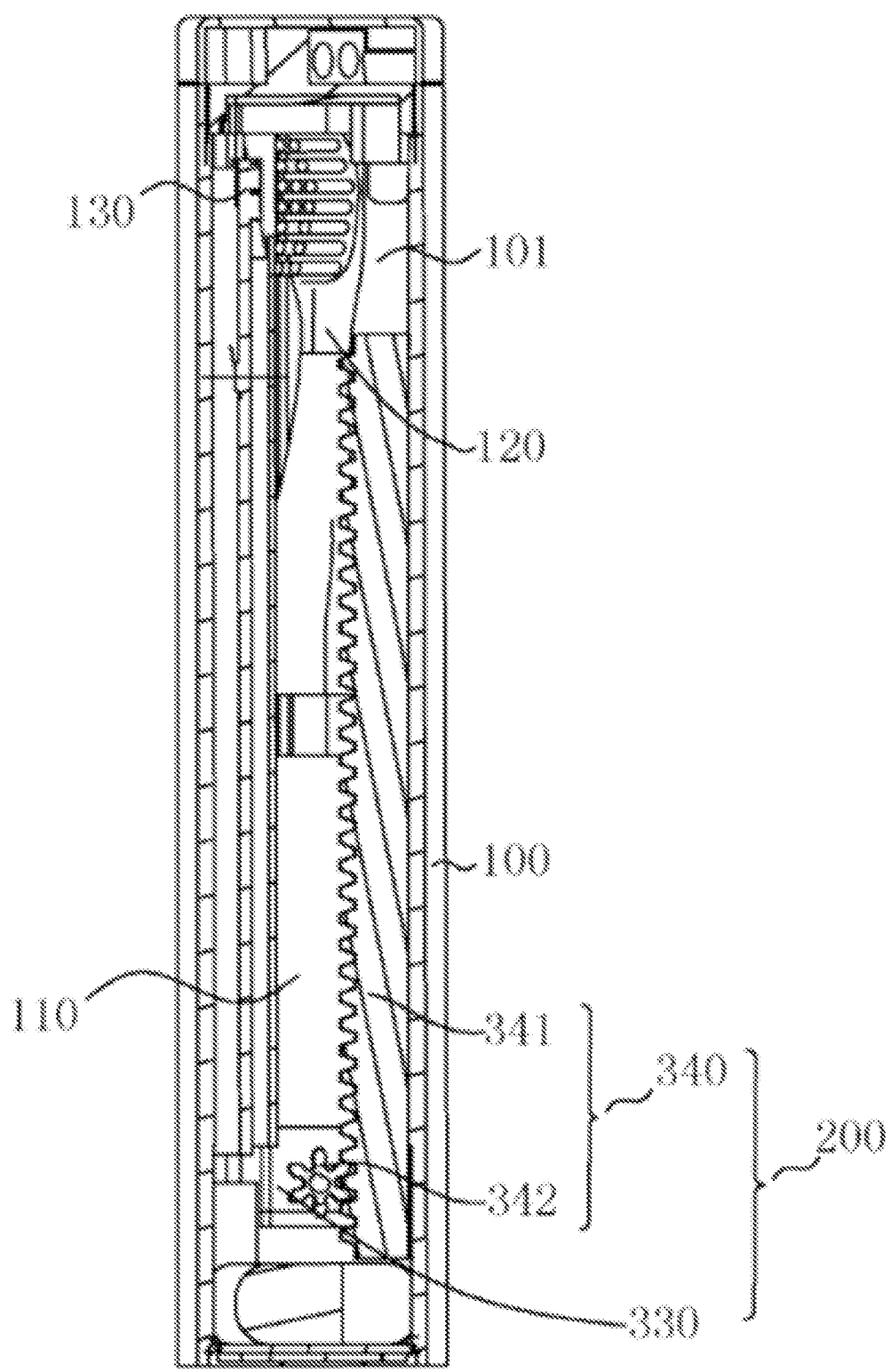
FIG. 9 is a schematic view of an internal structure of a disinfection device according to Embodiment 3.

FIG. 9 is a schematic view showing an internal structure of a disinfection device according to Embodiment 3. In this embodiment, the second driving portion 200 is provided with a second motor 330 and a gear and rack transmission mechanism 340, where the second motor 330 is mounted on the mounting portion 110. For the mounting of the second motor 330, reference can be made to the mounting mode of the first motor 230 in Embodiment 2. The difference is that in Embodiment 2, the output shaft of the first motor 230 is parallel to the sliding direction of the mounting portion 110, while in Embodiment 3, the output shaft of the second motor 330 is perpendicular to the sliding direction of the mounting portion 110. A rack 341 of the gear and rack transmission mechanism 340 is fixed in the first accommodating cavity 101, for example, mounted on the housing 100, and a gear 342 of the gear and rack transmission mechanism 340 is connected to the output shaft of the second motor 330. In addition, in this embodiment, a guide portion may be provided with reference to Embodiment 1 or Embodiment 2, and will not be described in detail here.

Embodiment 4

Figure 10:
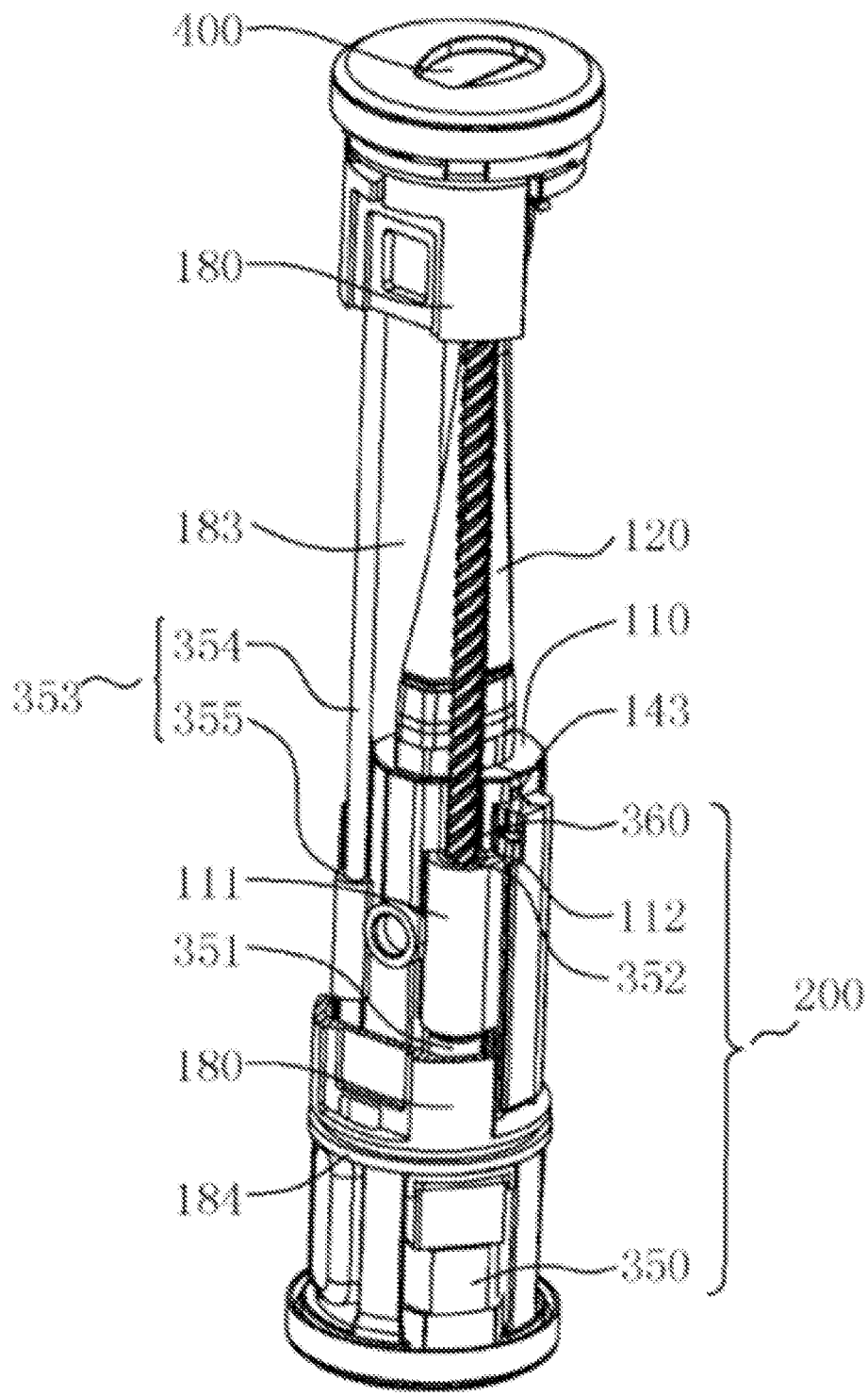
FIG. 10 is a schematic view of an internal structure of a disinfection device according to Embodiment 4 from one perspective.
Figure 11:
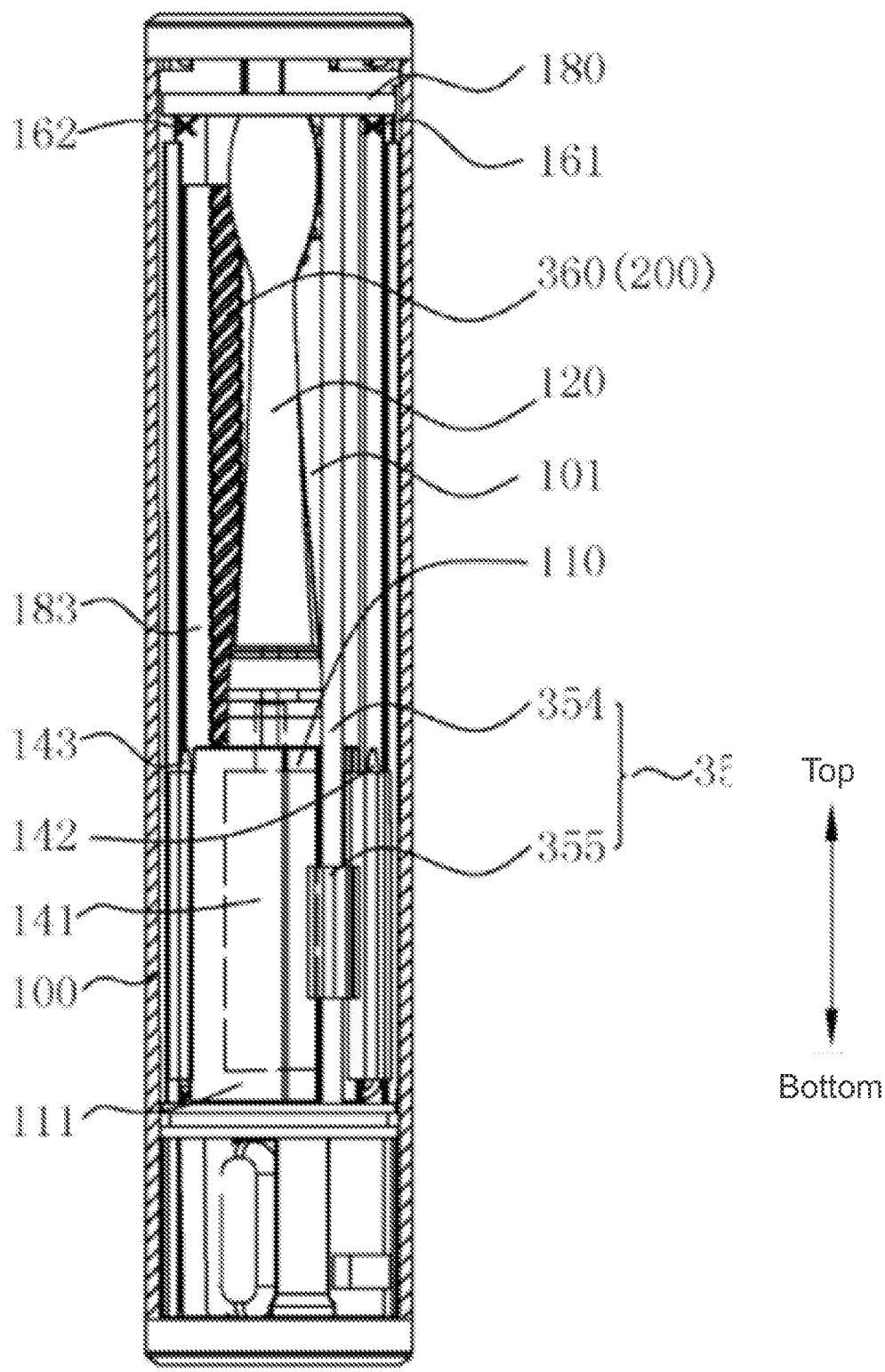
FIG. 11 is a schematic view of the internal structure of the disinfection device according to Embodiment 4 from another perspective.

FIG. 10 is a schematic view showing an internal structure of a disinfection device according to Embodiment 4 from one perspective. FIG. 11 is a schematic view showing the internal structure of the disinfection device according to Embodiment 4 from another perspective. Referring to FIG. 10 and FIG. 11, in this embodiment, the second driving portion 200 is provided with a third motor 350 and a screw 360, the third motor 350 is mounted on the housing 100, one end of the screw 360 is connected to the third motor 350, the mounting portion 110 is provided with a screw hole 112, and the screw 360 is engaged with the screw hole 112 of the mounting portion 110. It can be understood that herein, the description of mounting the third motor 350 on the housing 100 does not mean that the third motor 350 must be directly mounted on the housing 100, and the third motor 350 may alternatively be mounted on any component (such as the base 180) that is relatively fixedly connected to the housing.

Specifically, in this embodiment, with reference to Embodiment 1, a base 180 may be provided, the third motor 350 is directly mounted on the partition plate 184, and the screw 360 is arranged in the second mounting space 183. One end of the screw 360 is rotatably fixed to the upper portion of the base 180, and the other end of the screw 360 is connected to an output shaft (not shown) of the third motor 350 through a coupling 351. The screw hole 112 is formed in the mounting housing 111, the mounting housing 111 is provided with a nut mounting hole in which a nut 352 with the screw hole 112 is embedded, and the screw 360 is engaged with the nut 352. To guide the axial sliding of the mounting portion 110, a third guide portion 353 is further provided. The third guide portion 353 is provided with a third guide shaft 354 made of metal and a third guide hole 355. The third guide shaft 354 is fixed in the first accommodating cavity 101, the third guide hole 355 is formed in the mounting portion 110, and the third guide shaft 354 is slidably inserted into the third guide hole 355. Similarly, the third guide shaft 354 may also be made of, for example, stainless steel, such as SUS303/SUS304. The third guide shaft 354 is also arranged in the second mounting space 183. One end of the third guide shaft 354 is fixed to the upper portion of the base 180, and the other end of the third guide shaft 354 is fixed to the partition plate 184. The third guide hole 355 is directly formed in the mounting housing 111. Therefore, when the third motor 350 drives the screw 360 to rotate, the mounting portion 110 slides linearly along the third guide shaft 354. By providing the third guide shaft 354 to guide the mounting portion 110, the stability of the mounting portion 110 can be further improved. Certainly, this embodiment only illustrates the third guide portion 353 by way of example, and does not limit it. Any proper mechanism that can guide a linear transmission mechanism driven by the motor can be used.

Embodiment 5

Figure 12:
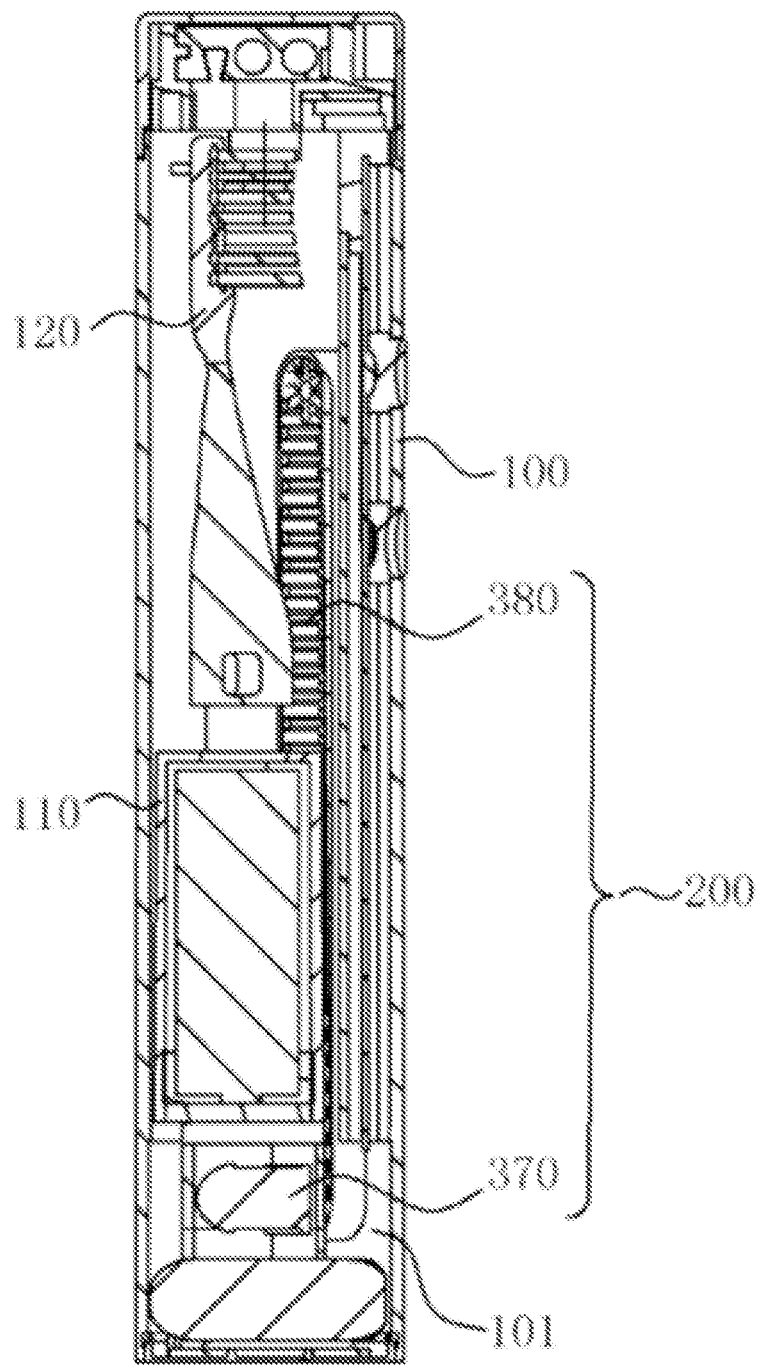
FIG. 12 is a schematic view of an internal structure of a disinfection device according to Embodiment 5.

FIG. 12 is a schematic view of an internal structure of a disinfection device according to Embodiment 5. In this embodiment, the second driving portion 200 is provided with a fourth motor 370 and a transmission belt 380. The fourth motor 370 is fixed in the first accommodating cavity 101, for example, mounted on the housing 100, and the transmission belt 380 is respectively connected to the fourth motor 370 and the mounting portion 110. It can be understood that herein, the description of mounting the third motor 350 on the housing 100 does not define that the third motor 350 must be directly mounted on the housing 100, and the third motor 350 may alternatively be mounted on any component that is relatively fixedly connected to the housing 100.

Embodiment 6

Figure 13:
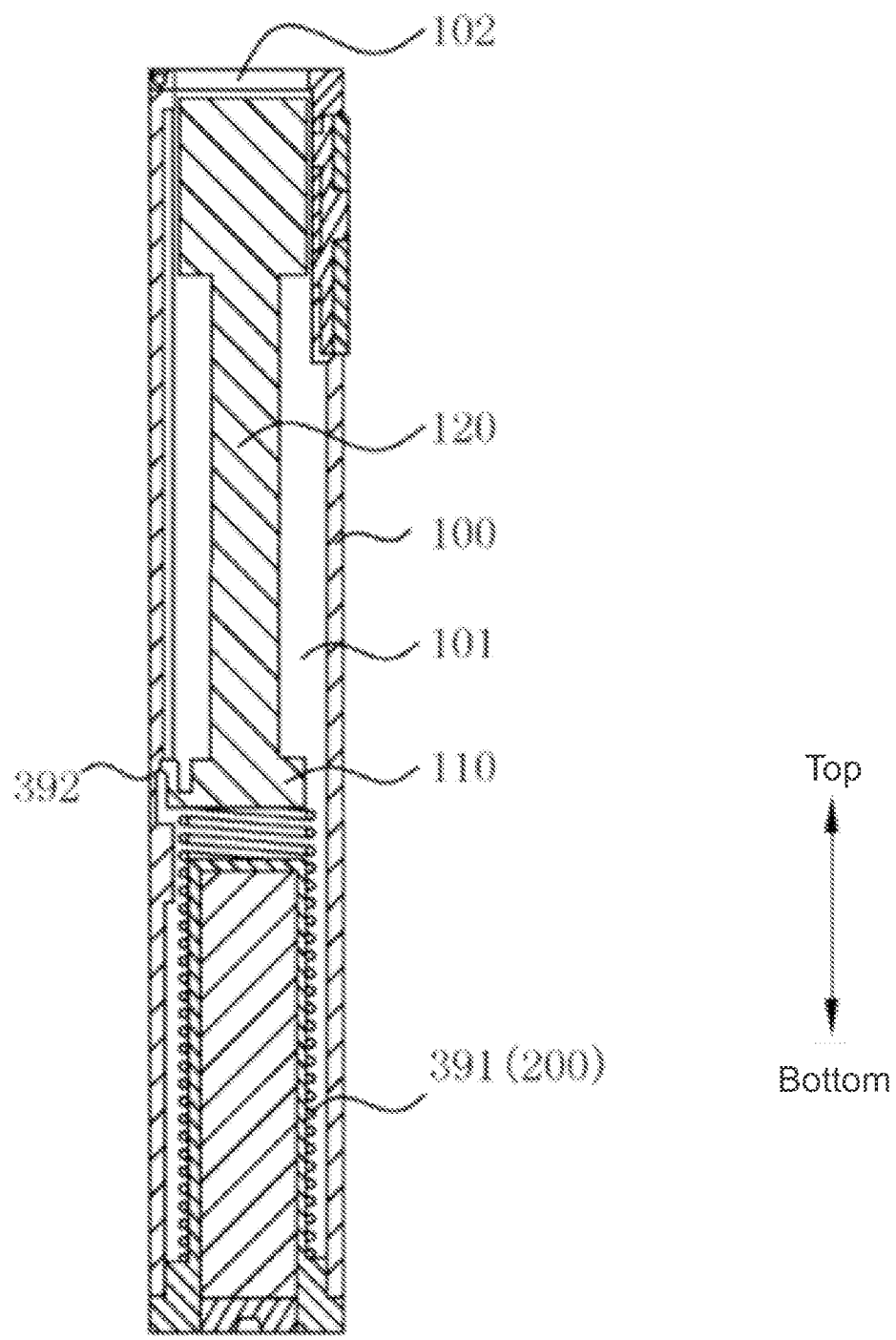
FIG. 13 is a schematic view of an internal structure of a disinfection device according to Embodiment 6.

FIG. 13 is a schematic view of an internal structure of a disinfection device according to Embodiment 6. Referring to FIG. 13, this embodiment differs from the previous embodiments in that in the second driving portion 200 a first spring 391 is used instead of a motor. Specifically, the first spring 391 is accommodated in the lower portion of the first accommodating cavity 101, and is configured to drive the mounting portion 110 to slide toward the upper portion of the first accommodating cavity 101, with one end abutting against the lower end of the housing 100 and the other end abutting against the lower portion of the mounting portion 110. To allow the toothbrush head 120 to be stably accommodated in the first accommodating cavity 101, the first accommodating cavity 101 is internally provided with a clamping portion 392 that is arranged on the inner surface of the housing 100. When the mounting portion 110 compresses the first spring 391 to cause the toothbrush head 120 to retract into the first accommodating cavity 101, the clamping portion 392 clamps the mounting portion 110. When the clamping portion 392 and the mounting portion 110 are separated from each other, the first spring 391 drives the toothbrush head 120 to extend out of the housing 100 through the first opening portion 102. The clamping portion 392 may be of a known buckle structure. For example, the housing 100 is provided with a groove the inner surface, and a protrusion is arranged on the mounting housing 111 of the mounting portion 110; and when the mounting portion 110 compresses the first spring 391 to cause the toothbrush head 120 to retract into the first accommodating cavity 101, the protrusion of the mounting housing 111 is clamped into the groove of the housing 100. In this embodiment, a guide structure of the mounting portion 110 may be provided with reference to the above embodiments.

Other structures of this embodiment will be described below.

With continued reference to FIG. 11, in this embodiment, the vibration motor 141 is configured to start working after the toothbrush head 120 extends out to the exterior of the housing 100 through the first opening portion 102. Specifically, a first contact 161 and a second contact 162 respectively connected to the control board 160 (with auxiliary reference to FIG. 4) are arranged on the upper portion of the first accommodating cavity 101, and a first electrode 142 and a second electrode 143 respectively connected to a vibration motor 141 are mounted on the mounting portion 110. When the second driving portion 200 drives the mounting portion 110 to slide to the upper portion of the first accommodating cavity 101, the first electrode 142 is in contact with the first contact 161, and the second electrode 143 is in contact with the second contact 162. Specifically, the first contact 161 and the second contact 162 are respectively mounted on the upper portion of the base 180, and the first electrode 142 and the second electrode 143 are respectively mounted on the mounting housing 111. When the second driving portion 200, for example, the motor of the second driving portion 200 drives the mounting housing 111 to slide to the upper portion of the first accommodating cavity 101, that is, after the toothbrush head 120 extends out in place, the first electrode 142 is in contact with the first contact 161, and the second electrode 143 is in contact with the second contact 162, so that the vibration motor 141 is powered on and thus can operate. Preferably, the first contact 161 and the second contact 162 are spring piece contacts. When the first electrode 142 is in contact with the first contact 161, the first contact 161 clamps the first electrode 142, while the second contact 162 clamps the second electrode 143 when the second electrode 143 is in contact with the second contact 162. The spring piece contact is arranged to clamp the electrode, which can prevent the poor contact caused by oxidation after the electrode is used for a long time, thereby improve the contact stability.

With continued reference to FIG. 2 to FIG. 4, in this embodiment, in order to limit the sliding stroke of the mounting portion 110 in the axial direction of the first accommodating cavity 101, limit switches 170 are arranged on the upper portion and the lower portion of the first accommodating cavity 101, respectively. The limit switches 170 can be either a contact mechanical switch or a non-contact switch, such as a photoelectric switch and a Hall switch. The limit switches 170 may be mounted on the upper portion of the base 180 and the partition plate 184, respectively.

Figure 14:
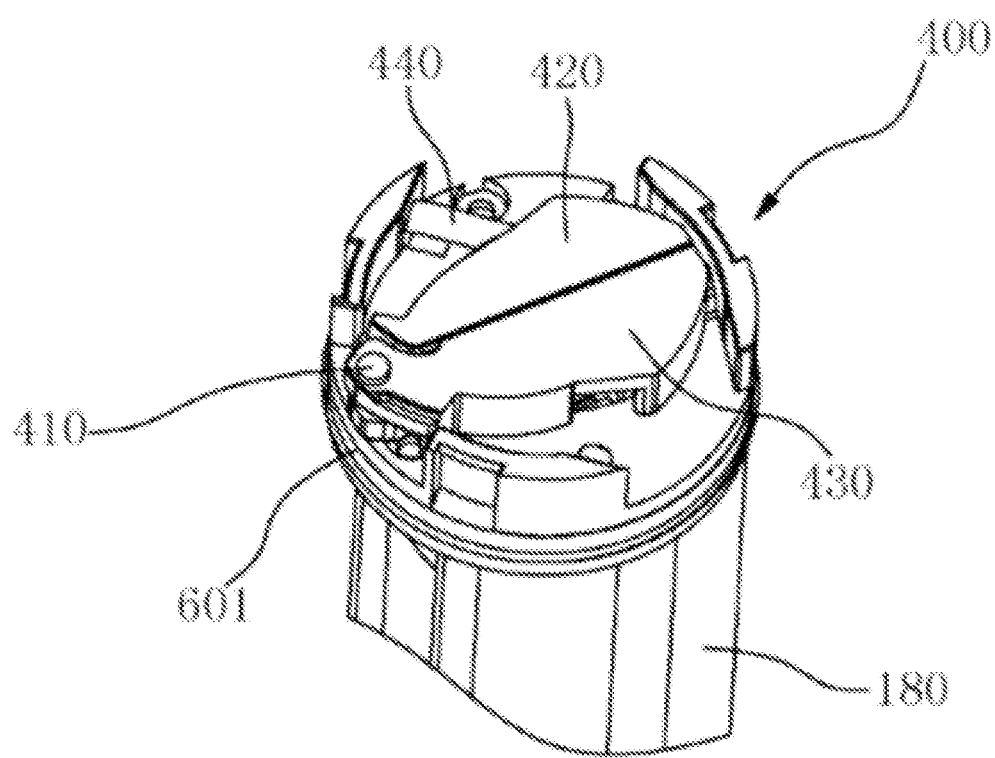
FIG. 14 is a perspective view of an upper cover portion.

FIG. 14 is a perspective view of an upper cover portion 400. With reference to FIG. 14, and with auxiliary reference to FIG. 2 and FIG. 3, in addition, in this embodiment, the disinfection device further includes the upper cover portion 400, which is configured to be capable of opening or closing the first opening portion 102. Through the arrangement of the upper cover portion 400 capable of opening or closing the first opening portion 102, when the disinfection lamp of the disinfection portion 130 is disinfected in the first accommodating cavity 101, the whole first accommodating cavity 101 is closed by covering the first opening portion 102, thereby preventing leakage of disinfection light. Moreover, when the disinfection device is used as a toothbrush, water stains can be prevented from penetrating into the first accommodating cavity 101 to a certain extent. The upper cover portion 400 is arranged at the upper end of the housing 100. Specifically, the upper cover portion 400 includes a hinge pin 410, a first cover body 420, a second cover body 430, and second springs 440. One end of the hinge pin 410 in the axial direction is mounted on the base 180, and the first cover body 420 and the second cover body 430 are respectively hinged to the joint pin 410 and rotate around the hinge pin 410 to approach or move away from each other. There are two second springs 440, which abut against the first cover body 420 and the second cover body 430 respectively to push the first cover body 420 and the second cover body 430 close to each other. When the second driving portion 200 drives the toothbrush head 120 to extend out, the toothbrush head 120 pushes the first cover body 420 and the second cover body 430 away from each other, so that the toothbrush head 120 extends out of the housing 100 through the first opening portion 102. After the second driving portion 200 drives the toothbrush head 120 to retract into the first accommodating cavity 101, the two second springs 440 drive the first cover body 420 and the second cover body 430 to rotate around the hinge pin 410 and close to each other, respectively, so that the first opening portion 102 is closed.

In addition, in order to charge the battery 150, a wireless charging coil 151 or other charging devices such as a USB charging port may further be provided at the bottom of the first accommodating cavity 101.

In addition, the outer periphery of the housing 100 is further provided with a power switch button and buttons for operating various components in the first accommodating cavity 101, such as the motor, the sterilizing lamp and the vibration motor 141.

The specific technical features described in the above specific embodiments can be combined in any way provided that no contradiction occurs. To avoid unnecessary repetition, various possible combination modes are not explained separately in the present invention.

The above embodiments are only used to illustrate the technical solutions of the present invention, but not intended to limit them. Any modification or equivalent replacement that does not depart from the scope of the present invention should be included in the technical solutions of the present invention.

What is claimed is:

1. A disinfection device, comprising:
a housing, having a first accommodating cavity within the housing, and a first opening portion at an upper end of the housing, and the first opening portion being communicated with the first accommodating cavity and capable of being opened or closed;
a mounting portion, accommodated in the first accommodating cavity and capable of sliding in an axial direction of the first accommodating cavity;
a disinfection portion, arranged in the first accommodating cavity and performing disinfection in the first accommodating cavity after the first opening portion is closed; and
a second driving portion, accommodated in the first accommodating cavity and connected to the mounting portion, wherein the second driving portion drives the mounting portion to slide in the axial direction of the first accommodating cavity;
wherein the second driving portion comprises:
a first sleeve, provided with an internal thread on an inner surface thereof, and the mounting portion being accommodated in the first sleeve;
an external thread portion, connected to the mounting portion and engaged with the internal thread of the first sleeve; and
a first motor, configured to drive the first sleeve and the external thread portion to rotate relatively.

2. The disinfection device of claim 1, wherein the mounting portion comprises a mounting housing, the external thread portion is arranged on an outer peripheral surface of the mounting housing, and the first motor is connected to the first sleeve and drives the first sleeve to rotate.

3. The disinfection device of claim 2, further comprising a first guide portion comprising a first guide shaft and a first guide hole, wherein the first guide shaft is mounted to the housing and accommodated in the first accommodating cavity, the first guide hole is formed in the mounting housing, and the first guide shaft is inserted into the first guide hole.

4. The disinfection device of claim 2, wherein the first motor is mounted below the first sleeve, the first sleeve is provided with a first connecting piece at a lower portion thereof, and the first motor has an output shaft connected to the first connecting piece.

5. The disinfection device of claim 2, further comprising a second sleeve, wherein the second sleeve is accommodated in the first accommodating cavity, and the first sleeve is embedded in the second sleeve.

6. The disinfection device of claim 1, wherein the second driving portion is further provided with a first rotating part, the external thread portion is arranged on an outer peripheral surface of the first rotating part, the first motor is accommodated in the first sleeve and mounted on the mounting portion, and the first rotating part is connected to the output shaft of the first motor.

7. The disinfection device of claim 6, further comprising a second guide portion comprising a first guide groove and a first slider, wherein the first guide groove is arranged on the inner surface of the first sleeve and extends in an axial direction of the first sleeve, and the first slider is arranged on the mounting portion and capable of sliding in the first guide groove.

8. The disinfection device of claim 6, wherein the mounting portion comprises a mounting housing having a mounting cavity in which the first motor is mounted, and the output shaft of the first motor extends out of the mounting housing.

9. The disinfection device of claim 6, wherein between an outer surface of the first sleeve and an inner surface of the housing, the first accommodating cavity has a third mounting space extending in the axial direction of the first accommodating cavity, and a battery is mounted in the third mounting space.

10. The disinfection device of claim 1, wherein the second driving portion comprises:
   a first spring, accommodated in a lower portion of the first accommodating cavity and configured to drive the mounting portion to slide toward an upper portion of the first accommodating cavity; and
   a clamping portion, arranged on the inner surface of the housing and configured to clamp the mounting portion when the mounting portion compresses the first spring and slides toward the lower portion of the first accommodating cavity.

11. The disinfection device of claim 1, wherein the disinfection portion comprises a disinfection lamp capable of emitting disinfection light, and the disinfection lamp is arranged on the upper portion of the first accommodating cavity.

12. The disinfection device of claim 11, wherein the disinfection lamp is a UVC band disinfection lamp.

13. The disinfection device of claim 12, further comprising a control board with a boosting circuit.

14. A toothbrush, comprising:
   a toothbrush head; and
   a disinfection device, comprising:
      a housing, having a first accommodating cavity within the housing, and a first opening portion at an upper end of the housing, and the first opening portion being communicated with the first accommodating cavity and capable of being opened or closed;
      a mounting portion, accommodated in the first accommodating cavity and capable of sliding in an axial direction of the first accommodating cavity;
      a disinfection portion, arranged in the first accommodating cavity and performing disinfection in the first accommodating cavity after the first opening portion is closed; and
      a second driving portion, accommodated in the first accommodating cavity and connected to the mounting portion, wherein the second driving portion drives the mounting portion to slide in the axial direction of the first accommodating cavity;
   wherein the second driving portion comprises:
   a first sleeve, provided with an internal thread on an inner surface thereof, and the mounting portion being accommodated in the first sleeve;
   an external thread portion, connected to the mounting portion and engaged with the internal thread of the first sleeve; and
   a first motor, configured to drive the first sleeve and the external thread portion to rotate relatively;
   wherein, the toothbrush head is mounted on the mounting portion;
   wherein, when the mounting portion slides towards the upper portion inside the first accommodating cavity, the toothbrush head drives the first opening portion to be opened and extends to the exterior of the housing; and
   wherein, when the mounting portion slides toward the lower portion of the first accommodating cavity, the toothbrush head retracts from the exterior of the housing into the first accommodating cavity and closes the first opening portion.

15. The toothbrush of claim 14, further comprising a first driving portion mounted in the mounting portion, wherein the toothbrush head is detachably mounted on the first driving portion; and
   wherein the first driving portion is provided with a vibration motor, and the toothbrush head is detachably mounted on an output shaft of the vibration motor.

* * * * *